United States Patent [19]
Kajino et al.

[11] Patent Number: 6,099,828
[45] Date of Patent: Aug. 8, 2000

[54] HAIR TREATMENT COMPOSITION COMPRISING A LACTAM COMPOUND AND A WATER-SOLUBLE MACROMOLECULE

[75] Inventors: Takayoshi Kajino; Hajime Tokuda; Yoshinori Saitoh; Akira Kiyomine, all of Tokyo, Japan

[73] Assignee: Kao Corporation, Tokyo, Japan

[21] Appl. No.: 09/077,876

[22] PCT Filed: Oct. 6, 1997

[86] PCT No.: PCT/JP97/03565

§ 371 Date: Jun. 8, 1998

§ 102(e) Date: Jun. 8, 1998

[87] PCT Pub. No.: WO98/15256

PCT Pub. Date: Apr. 16, 1998

[30] Foreign Application Priority Data

Oct. 8, 1996 [JP] Japan ................................. 8-287469
Oct. 8, 1996 [JP] Japan ................................. 8-287470
Nov. 12, 1996 [JP] Japan ................................. 8-316966
Dec. 25, 1996 [JP] Japan ................................. 8-357291

[51] Int. Cl.$^7$ ................................. A61K 7/13; A61K 7/06
[52] U.S. Cl. ................. 424/70.15; 424/70.1; 424/78.02; 132/208; 8/406; 8/409
[58] Field of Search ................................. 424/70.1, 78.02, 424/70.6, 70.15; 132/208; 8/406, 409

[56] References Cited

FOREIGN PATENT DOCUMENTS 3-294217 12/1991 Japan .
6-298625 10/1994 Japan .
60-228407 12/1996 Japan .
8-333224 12/1996 Japan .
95/20375 8/1995 WIPO .

Primary Examiner—Thurman K. Page
Assistant Examiner—Brian K. Seidleck
Attorney, Agent, or Firm—Oblon, Spivak, McClelland, Maier & Meustadt, P.C.

[57] ABSTRACT

A hair treatment composition comprising a compound of Formula (1):

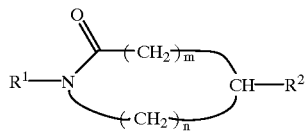

(1)

wherein $R^1$, $R^2$, m and n are as defined in the disclosure; and a water-soluble macromolecule.

7 Claims, No Drawings

HAIR TREATMENT COMPOSITION COMPRISING A LACTAM COMPOUND AND A WATER-SOLUBLE MACROMOLECULE

This application is a 371 of PCT/JP97/03565, filed Oct. 6, 1997.

TECHNICAL FIELD

This invention relates to a hair treatment composition that can maintain its conditioning effect over a long period of time. More particularly, this invention relates to a hair-coloring hair treatment composition that has superior dyeing properties, can impart a good feel to hair and also has a high safety to the hair and the skin.

BACKGROUND ART

Conventionally, the hair is physically or chemically treated in various manners. For example, it is often shampooed, dressed with a hairbrush, dried with a hair dryer, permed, decolored, and colored with a hair color.

However, such physical or chemical treatment causes the hair to be damaged, to become bristly or to be statically charged. Accordingly, in order to maintain beautiful and healthy hair against such treatment, it is necessary to prevent the hair from being damaged and keep it soft.

For this purpose, quaternary ammonium salts are conventionally added to hair treatment compositions such as hair rinses and hair treatments.

However, the adsorption of quaternary ammonium salts on the hair is due to a mere affinity of quaternary ammonium salts for the hair, resulting in an insufficient adsorptivity. Hence, such hair treatment compositions have a resistance to swimming, sweating or the like but have a problem that they are washed away as a result of washing such as shampooing.

Recently, for basically the same purpose as the addition of quaternary ammonium salt, water-soluble macromolecules such as cationic polymers and amphoteric polymers are added to shampoos. In the case of such shampoos, a cationic/anionic composite chiefly adheres to the hair's surface, and hence the water-soluble polymer does not well penetrate into a hair, resulting in an insufficient durability of conditioning effect. There has been also a problem that the conditioning effect is rather damaged when the hair treated with such a shampoo is rinsed with the above hair treatment composition.

Accordingly, hair treatment compositions such as hair rinses are conventionally mixed with benzyl alcohol in order to promote the penetration of the water-soluble macromolecules such as cationic polymers and amphoteric polymers to the inside of a hair. It is also proposed to mix the hair treatment compositions with N-methyl- or N-ethylpyrrolidone in order to promote the penetration of quaternary nitrogen-containing cellulose ether as a sort of the cationic polymers to the inside of a hair (Japanese Patent Application Laid-open No. 3-294217).

However, in the case when the hair is treated with the hair treatment composition making use of benzyl alcohol or N-methyl- or N-ethylpyrrolidone as a penetration promoter, not only the conditioning effect immediately after treatment can not be said sufficient but also there has been a problem that the durability of conditioning effect is poor.

Oxidation hair dyes, a sort of hair treatments having been put into general use, require to make a hydrogen peroxide act on the hair under alkaline conditions when used, and hence there is a danger of causing hair damage or primary skin irritation. Accordingly, it is attempted to develop hair dyes making use of acid dyes that may less affect the scalp and the hair.

As such an attempt, diethylene glycol monoethyl ether is used in hair dyes as a penetration promoter that promotes the penetration of the acid dye into a hair. The diethylene glycol monoethyl ether is relatively well effective for keeping the hair flexible, but has a problem of insufficient dyeing properties. Accordingly, it is a recent trend to use benzyl alcohol as the penetration promoter.

In Japanese Patent Application Laid-open No. 60-228407, it is proposed to use a hair dye composition comprised of a dopa analogue, a penetration promoter and an oxidizing agent, and in U.S. Pat. No. 3,933,422, to use a hair dye composition containing a metal-containing dye and a penetration promoter.

However, as the penetration promoter, benzyl alcohol can not still be said to provide sufficient dyeing properties, can not well keep the hair flexible, and also has been problematic in view of its allergy-causative properties.

In the case of the hair dye composition disclosed in Japanese Patent Application Laid-open No. 60-228407, an oxidizing agent is used to cause the dopa analogue to form color. Hence, the color formed lacks in tone variations, and also the use of an oxidizing agent has caused a problem of hair damage.

In the case of the hair dye composition disclosed in U.S. Pat. No. 3,933,422, it may seriously cause uneven dyeing and also the dye may insufficiently penetrate into a hair. Moreover, the use of metal (chromium or cobalt) has caused problems on the feel and safety.

DISCLOSURE OF THE INVENTION

The present invention solves the above problems caused in the prior art, and provides a hair treatment composition that can impart a sufficient conditioning effect to the hair and can maintain its conditioning effect over a long period of time. In particular, it is an object of the present invention to provide a hair treatment composition that can give variations of color tones, has superior dyeing properties, can impart a good feel to the hair and also has a high safety to the hair and the skin.

The present inventors have discovered that the above object can be achieved when a water-soluble macromolecule is used in combination with, in place of benzyl alcohol or N-methyl- or N-ethylpyrrolidone, a specific lactam compound having a higher penetration promoting action, thus they have accomplished the present invention. The have also discovered that a hair treatment composition that can achieve the intended dyeing effect can be obtained when the water-soluble macromolecule is used in combination with, in addition to the specific lactam compound, an acid dye and further optionally a specific penetration promoter, thus they have accomplished the present invention.

More specifically, the present invention provides a hair treatment composition comprising the following components (A) and (B):

(A) A compound of Formula (1)

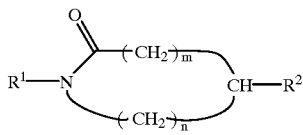

wherein $R^1$ represents (a) a hydrogen atom, (b) a straight-chain, branched or cyclic alkyl group or alkenyl group having 3 to 8 carbon atoms, (c) an aryl group or (d) a straight-chain, branched or cyclic alkyl group or alkenyl group having 1 to 8 carbon atoms, having in its backbone chain or side chain a substituent selected from the group consisting of an aryl group, a hydroxyl group, an ether group, an amide group, a carbonyl group and a carboxyl group; $R^2$ represents (a) a hydrogen atom, (b) a straight-chain, branched or cyclic alkyl group or alkenyl group having 1 to 8 carbon atoms, (c) an aryl group or (d) a straight-chain, branched or cyclic alkyl group or alkenyl group having 1 to 8 carbon atoms, having in its backbone chain or side chain a substituent selected from the group consisting of an aryl group, a hydroxyl group, an ether group, an amide group, a carbonyl group and a carboxyl group, provided that $R^1$ and $R^2$ are not hydrogen atoms at the same time; and n and m are integers that satisfy $2 \leq n+m \leq 4$; and (B) A water-soluble macromolecule.

BEST MODE FOR WORKING THE INVENTION

The hair treatment composition of the present invention will be described below in detail.

In the hair treatment composition of the present invention, at least one lactam compound represented by the following Formula (1) is used as component (A), which has the action to promote the penetration of component-(B) water-soluble macromolecule into a hair. These compounds have a better penetration promoting action than the penetration promoter benzyl alcohol or N-methyl- or N-ethylpyrrolidone.

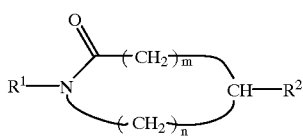

In the formula (1), $R^1$ represents (a) a hydrogen atom, (b) a straight-chain, branched or cyclic alkyl group or alkenyl group having 3 to 8 carbon atoms, (c) an aryl group or (d) a straight-chain, branched or cyclic alkyl group or alkenyl group having 1 to 8 carbon atoms, having in its backbone chain or side chain a substituent selected from the group consisting of an aryl group, a hydroxyl group, an ether group, an amide group, a carbonyl group and a carboxyl group; $R^2$ represents (a) a hydrogen atom, (b) a straight-chain, branched or cyclic alkyl group or alkenyl group having 1 to 8 carbon atoms, (c) an aryl group or (d) a straight-chain, branched or cyclic alkyl group or alkenyl group having 1 to 8 carbon atoms, having in its backbone chain or side chain a substituent selected from the group consisting of an aryl group, a hydroxyl group, an ether group, an amide group, a carbonyl group and a carboxyl group, provided that $R^1$ and $R^2$ are not hydrogen atoms at the same time; and n and m are integers that satisfy $2 \leq n+m \leq 4$.

In the compound of Formula (1), as preferred $R^1$, it may include (a) a hydrogen atom, (b) a straight-chain, branched or cyclic alkyl group having 3 to 8 carbon atoms, (c) an aryl group or (d) a straight-chain, branched or cyclic alkyl group having 1 to 8 carbon atoms, having at least one of an aryl group, a hydroxyl group and an ether group. As more preferred $R^1$, it may include (a) a hydrogen atom, (b) a straight-chain, branched or cyclic alkyl group having 3 to 8 carbon atoms, or (d) a straight-chain, branched or cyclic alkyl group having 1 to 8 carbon atoms, having at least one of an aryl group and an ether group.

In the compound of Formula (1), as preferred $R^2$, it may include (a) a hydrogen atom, (b) a straight-chain, branched or cyclic alkyl group having 1 to 8 carbon atoms, (c) an aryl group or (d) a straight-chain, branched or cyclic alkyl group having 1 to 8 carbon atoms, having at least one of an aryl group, a hydroxyl group and an ether group. As more preferred $R^2$, it may include (a) a hydrogen atom, (b) a straight-chain, branched or cyclic alkyl group having 1 to 8 carbon atoms, or (d) a straight-chain, branched or cyclic alkyl group having 1 to 8 carbon atoms, having at least one of an aryl group and an ether group.

Here, in $R^1$, as examples of the (b) straight-chain, branched or cyclic alkyl group having 3 to 8 carbon atoms, they may include a n-propyl group, a n-butyl group, a n-pentyl group, a n-hexyl group, a n-octyl group, a n-ethylhexyl group and a cyclohexyl group. As examples of the (c) aryl group, it may preferably include a phenyl group and a pyridyl group. As examples of the (d) straight-chain, branched or cyclic alkyl group having 1 to 8 carbon atoms, having in its backbone chain or side chain a substituent selected from the group consisting of an aryl group and an ether group, it may preferably include a benzyl group and an alkoxyalkyl group.

In $R^2$, as examples of the (b) straight-chain, branched or cyclic alkyl group having 1 to 8 carbon atoms, they may include a methyl group, an ethyl group, a n-propyl group, a n-butyl group, a n-pentyl group, a n-hexyl group, a n-octyl group, a n-ethylhexyl group and a cyclohexyl group. As examples of the (c) aryl group, it may preferably include a phenyl group and a pyridyl group. As examples of the (d) straight-chain, branched or cyclic alkyl group having 1 to 8 carbon atoms, having in its backbone chain or side chain a substituent selected from the group consisting of an aryl group and an ether group, it may preferably include a benzyl group and an alkoxyalkyl group.

Examples of the compound of Formula (1) in which the sum of m and n is 2 are shown in Table 1 below.

TABLE 1

| Compound of Formula (1) | Substituent | |
|---|---|---|
| | $R^1$ | $R^2$ |
| 2-methoxyethylpyrrolidone | 2-methoxyethyl | H |
| 3-methoxypropylpyrrolidone | 2-methoxypropyl | H |
| 3-hydroxypropylpyrrolidone | 2-hydroxypropyl | H |

TABLE 1-continued

| Compound of Formula (1) | Substituent | |
|---|---|---|
| | R¹ | R² |
| N-propylpyrrolidone | propyl | H |
| N-isopropylpyrrolidone | isopropyl | H |
| N-butylpyrrolidone | butyl | H |
| N-t-butylpyrrolidone | t-butyl | H |
| N-pentylpyrrolidone | pentyl | H |
| N-hexylpyrrolidone | hexyl | H |
| N-heptylpyrrolidone | heptyl | H |
| N-cyclohexylpyrrolidone | cyclohexyl | H |
| N-octylpyrrolidone | octyl | H |
| N-(2-ethylhexyl)pyrrolidone | 2-ethylhexyl | H |
| N-phenylpyrrolidone | phenyl | H |
| N-benzylpyrrolidone | benzyl | H |
| N-phenetylpyrrolidone | phenetyl | H |

As particularly preferred compounds among the compounds of Formula (1) listed in Table 1, they may include N-butylpyrrolidone, N-pentylpyrrolidone, N-hexylpyrrolidone, N-heptylpyrrolidone, N-octylpyrrolidone, N-(2-ethylhexyl)pyrrolidone, N-benzylpyrrolidone and N-phenetylpyrrolidone, and particularly include N-hexylpyrrolidone.

The component-(A) compound of Formula (1) may preferably be mixed in the hair treatment composition in an amount of from 0.01 to 30% by weight, because no sufficient penetration promoting effect can be obtained if mixed in a too small quantity and no higher penetration promoting effect can be expected if mixed in a too large quantity. In view of the conditioning effect, it may more preferably be in an amount of from 0.5 to 30% by weight, and particularly preferably from 1 to 20% by weight. When it is intended to make hair-coloring effect higher by using it in combination with an acid dye described later, it may preferably be in an amount of from 0.01 to 30% by weight, and more preferably from 0.1 to 20% by weight.

The component (B) that constitutes the hair treatment composition of the present invention will be described below.

The component (B) is a water-soluble macromolecule, which cover a hair or penetrates into a hair to prevent the hair from being damaged and keep it soft.

The component-(B) water-soluble macromolecule may usually be mixed in the hair treatment composition in an amount of from 0.01 to 20% by weight, because its addition can not be well effective if mixed in a too small quantity and can not be expected to be more effective if mixed in a too large quantity.

Such a component-(B) water-soluble macromolecule may include one or more kinds of polymers selected from cationic polymers or amphoteric polymers, and anionic polymers.

The component-(B) cationic polymers may include cationized cellulose derivatives, cationic starches, cationized guar gum derivatives, quaternary ammonium salt/acrylamide copolymers, quaternary ammonium salt polymerization products, quaternized polyvinyl pyrrolidone derivatives, and cationic silicone polymers.

Here, the cationized cellulose derivatives may preferably include compounds represented by the following Formula (2).

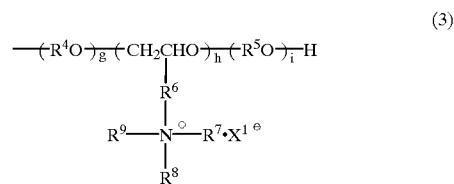

(2)

wherein A represents a residual group of an anhydroglucose unit, f is an integer of from 50 to 20,000; and $R^3$'s each represent a compound represented by the following Formula (3).

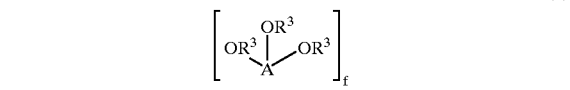

(3)

wherein $R^4$ and $R^5$ each independently represent an alkylene group having 2 or 3 carbon atoms; $R^6$ represents an alkylene group or hydroxyalkylene group having 1 to 3 carbon atoms; $R^7$, $R^8$ and $R^9$ each independently represent an alkyl group, aryl group or aralkyl group having not more than 20 carbon atoms, and any two of $R^7$, $R^8$ and $R^9$ may form a ring; g is an integer of from 0 to 10, h is an integer of from 0 to 3, and i is an integer of from 0 to 10; and $X^1$ represents an anion.

Such cationized cellulose derivatives may preferably have a degree of cation substitution (i.e., the average value of h per anhydroglucose unit) of from 0.01 to 1, and more preferably from 0.02 to 0.5, because no sufficient conditioning effect can be obtained if the degree is too low and the reaction yield may lower if the degree is too high, and may preferably have a molecular weight of from 100,000 to 8,000,000. Preferred combination of $R^7$, $R^8$ and $R^9$ may include an instance in which all of them are methyl group, and an instance in which any one of them is a long-chain alkyl group having 10 to 18 carbon atoms and the other two are short-chain alkyl groups having 1 to 3 carbon atoms. Also, the total of g and i is from 1 to 3 on the average. The anion represented by $X^1$ may include, e.g., chloride, bromide, iodide, sulfate, sulfonate, methyl sulfate, phosphate and nitrate ions.

The cationic starches may preferably include compounds represented by the following Formula (4).

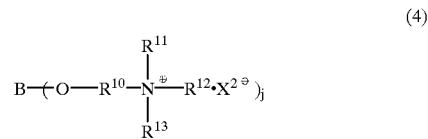

(4)

wherein B represents a starch residual group; $R^{10}$ represents an alkylene group or a hydroxyalkylene group; $R^{11}$, $R^{12}$ and $R^{13}$ each independently represent an alkyl group, aryl group or aralkyl group having not more than 10 carbon atoms, and any two of $R^{11}$, $R^{12}$ and $R^{13}$ may form a ring; i is a positive integer; and $X^2$ represents an anion.

Such cationic starches may preferably have a degree of cation substitution (i.e., the average value of j per anhydroglucose unit) of from 0.01 to 1, and more preferably from 0.02 to 0.5, because no sufficient conditioning effect can be obtained if the degree is too low and the reaction yield may lower if the degree is too high. The anion represented by $X^2$ may include, e.g., chloride, bromide, iodide, sulfate, sulfonate, methyl sulfate, phosphate and nitrate ions.

The cationized guar gum derivatives may preferably include compounds represented by the following Formula (5).

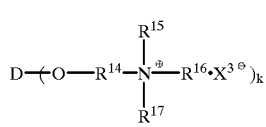

(5)

wherein D represents a guar gum residual group; $R^{14}$ represents an alkylene group or a hydroxyalkylene group; $R^{15}$, $R^{16}$ and $R^{17}$ each independently represent an alkyl group, aryl group or aralkyl group having not more than 10 carbon atoms, and any two of $R^{15}$, $R^{16}$ and $R^{17}$ may form a ring; k is a positive integer; and $X^3$ represents an anion.

Here, the cationized guar gum derivatives may preferably have a degree of cation substitution (i.e., the average value of k per sugar unit) of from 0.01 to 1, and more preferably from 0.02 to 0.5, because no sufficient conditioning effect can be obtained if the degree is too low and the reaction yield may lower if the degree is too high. The anion represented by $X^3$ may include, e.g., chloride, bromide, iodide, sulfate, sulfonate, methyl sulfate, phosphate and nitrate ions.

Such cationized guar gum derivatives are disclosed in, e.g., Japanese Patent Publications No. 58-35640 and No. 60-46158 and Japanese Patent Application Laid-open No. 58-53996, and are commercially available as products specified, e.g., as trade name "JAGUARL" (available from Seraniez Stein Hole Co.).

The cationic quaternary ammonium salt polymerization products or quaternary ammonium salt/acrylamide copolymers may preferably include compounds represented by the following Formula (6) or (7).

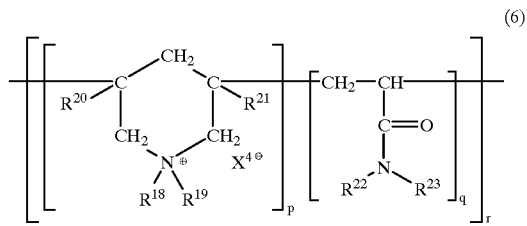

(6)

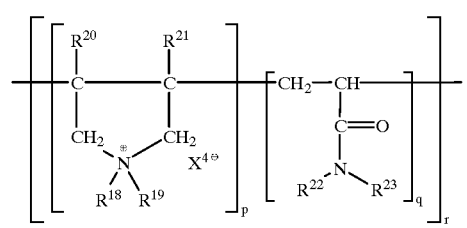

(7)

wherein $R^{18}$ and $R^{19}$ each independently represent a hydrogen atom, an alkyl group, phenyl group, aryl group, hydroxyalkyl group, amidoalkyl group, cyanoalkyl group, alkoxyalkyl group or carboalkoxyalkyl group having 1 to 18 carbon atoms; $R^{20}$, $R^{21}$, $R^{22}$ and $R^{23}$ each independently represent a hydrogen atom, an alkyl group having 1 to 3 carbon atoms or a phenyl group; p is an integer of from 1 to 50, q is an integer of from 0 to 50, r is an integer of from 150 to 8,000; and $X^4$ represents an anion.

Here, the quaternary ammonium salt/acrylamide copolymers may preferably have a molecular weight in the range of from about 30,000 to 2,000,000, and more preferably from 100,000 to 1,000,000. The anion represented by $X^4$ may include, e.g., chloride, bromide, iodide, sulfate, sulfonate, methyl sulfate, phosphate and nitrate ions.

The quaternized polyvinyl pyrrolidone derivatives may preferably include compounds represented by the following Formula (8).

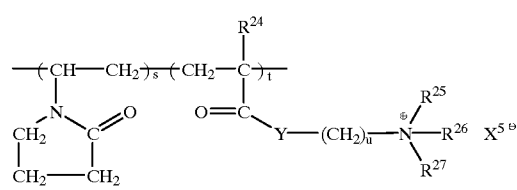

(8)

wherein $R^{24}$ represents a hydrogen atom, an alkyl group having 1 to 3 carbon atoms; $R^{25}$, $R^{26}$ and $R^{27}$ each independently represent a hydrogen atom, an alkyl group, hydroxyalkyl group, amidoalkyl group, cyanoalkyl group, alkoxyalkyl group or carboalkoxyalkyl group having 1 to 4 carbon atoms; u is an integer of from 1 to 10, and s and t are integers of from 20 to 8,000 in total; Y represents an oxygen atom or an NH group in the amide brond; and $X^5$ represents an anion.

Here, the quaternized polyvinyl pyrrolidone derivatives may preferably have a molecular weight of from 10,000 to 2,000,000, and more preferably from 50,000 to 1,500,000. The anion represented by $X^5$ may include, e.g., chloride, bromide, iodide, sulfate, sulfonate, 1 to 4 carbon-atom alkyl sulfate, phosphate and nitrate ions.

Cationic nitrogen originating from the cationic macromolecule contained in the above vinyl polymer may preferably be contained in an amount of from 0.004 to 0.2%, and more preferably from 0.01 to 0.15%, based on the vinyl polymer, because no sufficient conditioning effect can be obtained if it is in a too small content and the reaction yield may lower if it is in a too large content.

The cationic silicone polymers may preferably include a compound represented by the following Formula (9) and having an average molecular weight of from about 3,000 to 100,000.

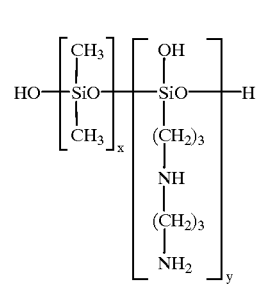

(9)

wherein x and y each represent an integer depending on the molecular weight.

This compound is disclosed in CTFA Dictionary (Cosmetic Ingredient Dictionary, 3rd Edition, USA) as a product named amodimethicone).

Such a cationic silicone polymer may preferably be used in the form of an aqueous emulsion. This aqueous emulsion is obtained by, e.g., subjecting i) an organodialkoxysilane having an aminoalkyl group and a hydroxyl group, a hydroxyalkyl group, an oxyalkylene group or a polyoxyalkylene group and ii) a cyclic diorganopolysiloxane to emulsion polymerization in the presence of a quaternary ammonium salt type surfactant and water, according to the method disclosed in Japanese Patent Publication No. 56-38609.

As the component-(B) amphoteric polymer, a polymer may be used which is produced by copolymerizing an acidic vinyl monomer and a basic vinyl monomer, by copolymerizing amphoteric monomers, or by introducing an acidic group, a basic group, both the acidic group and the basic group, or an amphoteric group into a synthetic or natural macromolecule according to its properties.

As typical examples of such an amphoteric polymer, it may include the following (aa) and (bb).

(aa) Copolymers of an acidic vinyl monomer with a basic vinyl monomer:

As typical examples of such copolymers, they may include those obtained by copolymerizing a monomer mixture comprised of 45 to 55 mol % of an acidic vinyl monomer or a salt thereof and 45 to 55 mol % of a basic vinyl monomer or a salt thereof in the presence of a known radical polymerization initiator at about 150° C. During the copolymerization, a known accelerator may be brought into presence. The above value of mol % is a numerical value given on condition that each vinyl monomer has one acidic group or basic group in the molecule. In the case of a monomer having a plurality of acidic groups or basic groups in the molecule, the mol % may be appropriately adjusted so that the net electric charge may come to be substantially zero.

Here, the acidic vinyl monomer refers to a compound having an acidic group such as a carboxyl group, a sulfonic acid group or a phosphoric acid group and a polymerizable vinyl group in the molecule. Such an acidic vinyl monomer may include unsaturated monobasic acids such as acrylic acid, methacrylic acid, crotonic acid, vinylbenzoic acid, 2-acrylamido-2-methylpropanesulfonic acid, styrenesulfonic acid, vinylsulfonic acid, allylsulfonic acid, methacrylsulfonic acid and 3-methacrylpropanesulfonic acid; unsaturated dibasic acids such as itaconic acid, maleic acid and fumaric acid; and monoesters of any of these. The salt thereof may include sodium salt, potassium salt and ammonium salt.

The basic vinyl monomer also refers to a compound having a basic group such as a primary amino group, a secondary amino group or a tertiary amino group and a polymerizable vinyl group in the molecule. Such a basic vinyl monomer may include dimethylaminoethyl methacrylate, diethylaminoethyl methacrylate, dimethylaminoethyl acrylate, diethylaminoethyl acrylate, dimethylaminopropyl acrylate, dimethylaminopropyl methacrylamide, dimethylaminopropyl acrylamide, 2-vinylpyridine, 4-vinylpyridine, dimethylallylamine, diallylmethylamine, and quaternized products of these. Here, as examples of the quaternized products, they may include hydroxides, methylated products, ethylated products, and mixed compounds of any of these. In this instance, counter anions of the quaternized products may include halide ions such as chloride ion and bromide ion, hydroxide ion, and methyl sulfate ion.

In this copolymerization, besides the acidic vinyl monomer and the basic vinyl monomer, other vinyl monomer copolymerizable with these may also be copolymerized as a third component. This other vinyl monomer may include monovinyl compounds copolymerizable in the presence of a radical polymerization initiator, as exemplified by acrylates such as methyl acrylate and ethyl acrylate, methacrylates such as methyl methacrylate and ethyl methacrylate, styrene compounds such as styrene and α-methylstyrene, acrylamide, methacrylamide, vinyl ether, and vinyl acetate. This other vinyl monomer may preferably be used in a proportion controlled to be not more than 60 mol% of the total monomers.

(bb) Copolymers of amphoteric monomers:

Such polymers may include those obtained by polymerizing amphoteric monomers represented by the following Formula (1), in the presence of a radical polymerization initiator at a temperature ranging from 20 to 130° C.

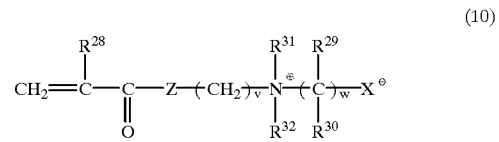

wherein $R^{28}$, $R^{29}$ and $R^{30}$ each independently represent a hydrogen atom or a methyl group; $R^{31}$ and $R^{32}$ each independently represent a methyl group or an ethyl group; Z represents —O— or —NH—; X represents —$CO_2$, —$SO_3$ or $PHO_3$; and v and w are each an integer of from 1 to 3.

Here, the amphoteric monomers represented by Formula (10) can be synthesized by allowing an aminoalkyl ester or aminoalkyl amide of the corresponding acrylic acid (or methacrylic acid) to react with lactone, sultone or a cyclic phosphide. Such amphoteric monomers may include, e.g., 3-dimethyl(methacryloyloxyethyl) ammonium propane sulfonate, and 3-dimethyl(methacryloylamidopropyl) ammonium propane sulfonate.

In this copolymerization, besides the amphoteric monomer, other vinyl monomer copolymerizable with it may also be copolymerized as an optional component. Such other vinyl monomer may include monovinyl compounds copolymerizable in the presence of a radical polymerization initiator, as exemplified by acrylates such as methyl acrylate and ethyl acrylate, methacrylates such as methyl methacrylate and ethyl methacrylate, styrene compounds such as styrene and α-methylstyrene, acrylamide, methacrylamide, vinyl ether, and vinyl acetate. This other vinyl monomer may preferably be used in a proportion controlled to be not more than 60 mol % of the total monomers.

When the above cationic polymer or amphoteric polymer is used as the component-(B) water-soluble macromolecule, these may be used alone or in combination of two or more. This component may preferably be mixed in the hair treatment composition in an amount of from 0.01 to 10% by weight, and more preferably from 0.1 to 5% by weight, because no sufficient conditioning effect can be obtained if it is in a too small quantity and any more conditioning effect can not be expected if it is in a too large quantity.

As the anionic polymer used as the component-(B) water-soluble macromolecule, either of natural anionic polymers and synthetic anionic polymers may be used.

As examples of the natural anionic polymers, they may include xanthane gum, caraginan, sodium alginate, pectin, furceran, gum arabic, gutch gum, caraya gum, tragacanth gum, agar powder. They may also include carboxymethyl cellulose obtained by carboxymethylation of cellulose.

As examples of the synthetic anionic polymers, they may include polymers obtained by polymerizing acidic vinyl monomers or salts thereof. Here, the acidic vinyl monomer refers to a compound having an acidic group such as a carboxyl group, a sulfonic acid group or a phosphoric acid group and a polymerizable vinyl group in the molecule. As examples thereof, they may include unsaturated monobasic acids such as acrylic acid, methacrylic acid, crotonic acid, vinylbenzoic acid, 2-acrylamido-2-methylpropanesulfonic acid, styrenesulfonic acid, vinylsulfonic acid, allylsulfonic acid, methacrylsulfonic acid and 3-methacrylopropanesulfonic acid; unsaturated dibasic acids such as itaconic acid, maleic acid and fumaric acid; and salts thereof such as alkali metal salts such as sodium salt or potassium salt, and ammonium salts.

When the anionic polymer is used as the component-(B) water-soluble macromolecule, it may be used alone or in combination of two or more. This component may preferably be mixed in the hair treatment composition in an amount of from 0.01 to 10% by weight, and more preferably from 0.1 to 5% by weight, because no sufficient conditioning effect can be obtained if it is in a too small quantity and any more conditioning effect can not be expected if it is in a too large quantity.

In the case when the hair treatment composition of the present invention is used in combination with the acid dye described later, so as to be used as a hair-coloring hair treatment composition, it is preferable to use as the component-(B) water-soluble macromolecule an anionic or nonionic water-soluble macromolecule including cellulose type water-soluble macromolecules such as hydroxyethyl cellulose, methyl cellulose, carboxymethyl cellulose and hydroxypropyl cellulose; gum type water-soluble macromolecules such as xanthane gum, guar gum, Pullulan, pectin, tamarind seed, tragacanth gum and gum arabic; a starch type water-soluble macromolecules such as starch, dextrin, carboxymethyl starch and dialdehyde starch, natural type water-soluble macromolecules such as sodium alginate; and synthetic type water-soluble macromolecules such as sodium polyacrylate, carboxyvinyl polymer, polyvinyl alcohol and polyvinyl pyrrolidone. Of these, cellulose type water-soluble macromolecules and gum type water-soluble macromolecules are preferred. Any of these water-soluble macromolecules may be used alone or in combination of two or more. Such a water-soluble macromolecule may preferably be contained in the hair treatment composition in an amount of from 0.05 to 20% by weight, and more preferably from 0.1 to 10% by weight, because it becomes difficult to impart a sufficient flexibleness to the hair if it is in a too small content and there is a possibility of resulting in an unpreferable feel of the hair if it is in a too large content.

In addition to the components (A) and (B) described above, the hair treatment composition of the present invention may be incorporated with any known hair function components. For example, for the purpose of changing color tones of the hair, a known direct dye may be incorporated as component (C). Like the component-(B) water-soluble macromolecule such as the cationic polymer or anionic polymer, the direct dye also deeply penetrates into a hair.

Such a direct dye may include, e.g., as nitro type dyes, 3-amino-4-hydroxynitrobenzene, 2-amino-5-hydroxynitrobenzene, 2-amino-3-hydroxynitrobenzene, 2-amino-5-N,N-bis-β-hydroxyethylaminonitrobenzene, 2-amino-4-chloro-5-N-β-hydroxyethylaminonitrobenzene, 2-amino-4-methyl-5-N-β-hydroxyethylaminonitrobenzene, 3,4-bis(N,β-hydroxyethylamino)nitrobenzene, 2-amino-4-methyl-5-N-β-γ-dihydroxypropylaminonitrobenzene, 2-amino-4-methyl-5-β-aminoethylaminonitrobenzene, 2-amino-4-hydroxynitrobenzene, and, as particularly advantageous ones, 3,4-diaminonitrobenzene, 2,5-diaminonitrobenzene, 2-amino-5-β-N-hydroxyethylaminonitrobenzene, 2-N-β-hydroxyethylamino-5-N,N-bis-β-hydroxyethylaminonitrobenzene, 2-N-methylamino-5-N,N-bis(β-hydroxyethyl)aminonitrobenzene, 2-N-methylamino-5-N-methyl-N-β-hydroxyethylaminonitrobenzene, 2-N-β-hydroxyethylamino-5-hydroxynitrobenzene, 3-methoxy-4-N-β-hydroxyethylaminonitrobenzene, (4-nitro-3-methylamino)phenoxyethanol, 2-N-β-hydroxyethylamino-5-aminonitrobenzene, 2-N-β-hydroxyethylaminonitrobenzene, 3-amino-4-N-β-hydroxyethylaminonitrobenzene, 3-β-hydroxyethoxy-4-N-β-hydroxyethylaminonitrobenzene, 2-amino-5-N-methylaminonitrobenzene, 2-amino-3-methylnitrobenzene, 2-N-β-hydroxyethylamino-5-β,γ-dihydroxypropoxynitrobenzene, 3-hydroxy-4-N-β-hydroxyethylaminonitrobenzene, 3-hydroxy-4-aminonitrobenzene, 2,5-N,N -β-hydroxyethylaminonitrobenzene, 2-N-methylamino-4-methylamino-4-o-β,γ-dihydroxypropoxynitrobenzene, 2-N-β-aminoethylamino-5-N,N -bis(β-hydroxyethyl)aminonitrobenzene, 2-N-β-aminoethylamino-4-methoxynitrobenzene, 2-N-β-aminoethylamino-5-β-hydroxyethoxynitrobenzene, 1-amino-4-methylaminoanthraquinone, and 1,4-diaminoanthraquinone; as acid dyes, nitro dyes, azo dyes, nitroso dyes, triphenylmethane dyes, xanthene dyes, quinoline dyes, anthraquinone dyes and indigo dyes (stated specifically, Red No. 2 (C.I. No. 16185), Red No. 3 (C.I. No. 45430), Red No. 102 (C.I. No. 16255), Red No. 104 (C.I. No. 45410), Red No. 105 (C.I. No. 45440), Red No. 106 (C.I. No. 45100), Yellow No. 4 (C.I. No. 19140), Yellow No. 5 (C.I. No. 15985), Green No. 3 (C.I. No. 42053), Blue No. 1 (C.I. No. 42090), Blue No. 2 (C.I. No. 73015), Red No. 201 (C.I. No. 15850), Red No. 227 (C.I. No. 17200), Red No. 220 (C.I. No. 15880), Red No. 230 (C.I. No. 45380), Red No. 231 (C.I. No. 45410), Red No. 232 (C.I. No. 45440), Orange No. 205 (C.I. No. 15510), Orange No. 207 (C.I. No. 45425), Yellow No. 202 (C.I. No. 45350), Yellow No. 203 (C.I. No. 47005), Green No. 201 (C.I. No. 61570), Green No. 204 (C.I. No. 59040), Green No. 205 (C.I. No. 42095), Blue No. 202 (C.I. No. 42052), Blue No. 203 (C.I. No. 42052), Blue No. 205 (C.I. No. 42090), Brown No. 201 (C.I. No. 20170), Red No. 401 (C.I. No. 45190), Red No. 502 (C.I. No. 16155), Red No. 503 (C.I. No. 16150), Red No. 504 (C.I. No. 14700), Red No. 506 (C.I. No. 15620), Orange No. 402 (C.I. No. 14600), Yellow No. 402 (C.I. No. 18950), Yellow No. 403 (C.I. No. 10316), Yellow No. 406 (C.I. No. 13065), Yellow No. 407 (C.I. No. 18820), Green No. 401 (C.I. No. 10020), Green No. 402 (C.I. No. 42085), Violet No. 401 (C.I. No. 60730), Black No. 401 (C.I. No. 20470), etc.); as oil-soluble dyes, Red No. 215, Red No. 218, Red No. 225, Orange No. 201, Orange No. 206, Yellow No. 201, Yellow No. 204, Green No. 202, Violet No. 201, Red No. 501, Red No. 505, Orange No. 403, Yellow No. 404, Yellow No. 405, and Blue No. 403; as disperse dyes, Red No. 215, Red No. 218, Red No. 223, Red No. 225, Orange No. 201, Orange No. 206, Yellow No. 201, Yellow No. 204, Green No. 202, Violet No. 201, Red No. 501, Red No. 505, Yellow No. 404, Yellow No. 405, and Blue No. 403; as basic dyes, Red No. 213 and Red No. 214; and as basic dyes available from Willams Co., Sienna Brown, Mahogany, Madder Red, Steel Blue, and Straw Yellow. Of these direct dyes, the acid dye may preferably be used as the component (C), which may less adversely affect the scalp and the hair.

Such an acid dye may preferably be contained in the hair-coloring hair treatment composition in am amount of from 0.0001 to 10% by weight, and more preferably from 0.01 to 1% by weight, because the dyeing properties may be insufficient if it is in a too small content and, if it is in a too large content, there is a possibility of a lowering of solubility and also there can be no effect enough for its addition in such a quantity.

In order to modify the feel to the hair, the hair treatment composition of the present invention may also preferably be incorporated with an anionic surfactant, ampholytic surfactant or betaine type surfactant of various types which is capable of forming a complex with the component (B) when the cationic polymer or amphoteric polymer are used as the component-(B) water-soluble macromolecule. Any of these surfactants may be used alone or in combination. As examples of these surfactants, they may include straight-chain or branched alkylbenzene sulfonates, alkyl or alkenyl sulfates, ethylene oxide and/or propylene oxide addition alkyl or alkenyl ether sulfates, olefin sulfonates, alkane sulfonates, saturated or unsaturated fatty acid salts, ethylene oxide and/or propylene oxide addition alkyl or alkenyl ether carboxlates, α-sulfofatty esters, amino acid type surfactants such as amidoamino acid and acylated amino acid, phosphoric ester type surfactants, sulfosuccinic acid type surfactants, taurine type surfactants, amide ether sulfate type surfactants, sulfonic acid type surfactants, carbobetaine type surfactants, sulfobetaine type surfactants, and amidobetaine type surfactants.

In the case when the anionic polymer is used as the component-(B) water-soluble macromolecule, the hair treatment composition may preferably be incorporated with a cationic surfactant, ampholytic surfactant or betaine type surfactant of various types which is capable of forming a complex with the component (B). Any of these surfactants may be used alone or in combination.

The cationic surfactant may preferably include quaternary ammonium salts represented by Formula (11).

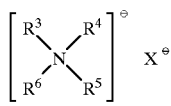

(11)

wherein one or two of $R^3$, $R^4$, $R^5$ and $R^6$ is/are each a straight-chain or branched alkyl group or hydroxyalkyl group having 8 to 22 carbon atoms, and others are each an alkyl group having 1 to 3 carbon atoms, a hydroxyalkyl group having 1 to 3 carbon atoms, a benzyl group or a polyoxystyrene group whose number of moles added is not more than 10 in total; and X is a halogen atom or an alkylsulfate group having 1 or 2 carbon atoms. As examples thereof, it may include trimethylammonium stearyl chloride, dimethylammonium distearyl chloride, trimethylammonium behenyl chloride, dimethylbenzylammonium cetyl chloride, benzylmethylammonium stearyl chloride, alkyltrimethylammonium beef tallow chlorides, trimethylammonium 2-octyldodecyl chloride, trimethylammonium 2-hexyldecyl chloride, and dimethylammonium branched dialkyl chlorides.

The ampholytic surfactant may preferably include amidoamino acids, and the betaine type surfactant may preferably include carbobetaine type surfactants, sulfobetaine type surfactants and amidobetaine type surfactants.

In the hair treatment composition of the present invention, at least one of ethylene carbonate and propylene carbonate may preferably be used as component (D), serving as an auxiliary agent (penetration promoting auxiliary) for increasing the penetration promoting action of the component-(A) lactam compound. In particular, this addition is remarkably effective when used in combination with the acid dye.

In the present invention, the ethylene carbonate and propylene carbonate may preferably be contained in the hair treatment composition in an amount of from 0.1 to 30% by weight in total, and more preferably from 0.5 to 20% by weight in total, because the penetration promoting action may be insufficient if it is in a too small content and a uniform mixture system may be obtained with difficulty if it is in a too large content.

The hair treatment composition of the present invention, when used in combination with the acid dye so as to be used for hair coloring, may damage dyeing properties of the acid dye if it has a too high pH. Accordingly, its pH may preferably be adjusted to 2 to 6, and more preferably from 2 to 4. In this instance, the pH may be adjusted with, e.g., an organic acid such as lactic acid, tartaric acid, acetic acid, citric acid or oxalic acid, or an inorganic acid such as phosphoric acid or hydrochloric acid. Various additives, e.g., lower alcohols, anticeptics, chelating agents and perfumes, used in usual hair treatment compositions may be further mixed so long as the stability of the system is not damaged and the pH value is kept within that range.

In the case when the hair treatment composition of the present invention is used for hair coloring, the composition may preferably contain water (preferably purified water or ion-exchanged water) as the balance other than the components (A), (B), acid dye, acid for pH adjustment and other components optionally added. Here, the water may be contained in the hair treatment composition in an amount of from 10 to 97% by weight, which may vary depending on the content of other components.

In addition to the above components, the hair treatment composition of the present invention may be incorporated with a solvent in order to improve the solubility of the components (A) and (B); the solvent including lower alcohols such as ethanol, n-propanol and isopropanol, alkylene glycols such as propylene glycol, dialkylene glycols, and trialkylene glycols, or alkyl ethers or alkylamide derivatives thereof.

The hair treatment composition of the present invention may be appropriately mixed with a thickening agent such as hydroxyethyl cellulose, a feel improver such as silicone, a perfume, an anticeptic, an ultraviolet light absorber, an antioxidant, a germicide and so forth which are usually used in cosmetics.

The hair treatment composition of the present invention can be prepared by uniformly dissolving or dispersing the components (A) and (B) and further optionally other components by a known method.

The hair treatment composition of the present invention may preferably be used as hair packs, hair dyes, hair treatments, hairstyling preparations, permanent waves, hair colors, hair bleaches, shampoos, hair rinses and so forth. Especially when used for hair coloring, it may preferably be furnished in the form of creams, emulsions, gels, solutions, mousse or foams.

To prepare the composition in the form of creams, emulsions, gels or solutions, for example, a wetting agent (an emulsifier), a solubilizing agent, a stabilizer, a feel improver, a hair-conditioning base, a perfume and so forth which are usually used in the field of cosmetics may be added to the hair treatment composition of the present invention and made into products by conventional methods. The wetting agent (emulsifier) used here may include, e.g., anionic, ampholytic and nonionic surfactants such as alkylbenzene sulfonates, fatty alcohol sulfates, alkyl sulfonates, acylated amino acids, fatty acid Alkanol amides, and ethylene oxide/fatty alcohol addition products. The feel improver and the hair-conditioning base may include, e.g., oily components such as silicone derivatives, higher alcohols and various nonionic surfactants, and cationic surfactants.

To prepare the composition in the form of mousse or foams, for example, a mixture prepared by adding 1% by weight or more of a usual surfactant (e.g., nonionic type) and 0.5 to 1% by weight of a thickening agent to the hair treatment composition of the present invention may be packed into aerosol cans together with a liquefied propelling gas (a propellant) such as chrolofluorocarbon gas or propane gas so that the mixture can be ejected in the form of foams when used.

When the hair treatment composition is applied to the hair, the hair treatment composition of the present invention may preferably be, after it has been applied to the hair, heated at 30 to 45° C. for 10 to 35 minutes in order to make it more effective. Also, when keratinous fibers such as the hair are dyed, the hair treatment composition of the present invention may be applied to the keratinous fibers at 15 to 50° C. and, after the composition is left to act for 10 to 30 minutes, the keratinous fibers thus treated may be washed and then dried.

As described above, upon treatment of the hair with the hair treatment composition of the present invention, the component (A) causes a hair to swell to thereby promote the penetration of the component (B) into a hair. Thus, the hair-coloring hair treatment composition may be applied to the hair and the hair thus treated may be washed and then dried, whereupon the composition well penetrates into a hair to well color the hair and at the same time keeps the hair moist and smooth.

EXAMPLES

The present invention will be described below in greater detail by giving Examples.

Examples 1 to 7, Comparative Examples 1 to 5

Hair treatment compositions having the formulation as shown in Tables 2 and 3 were prepared by conventional methods.

In respect of each hair treatment composition thus obtained, the conditioning effect brought about when applied to the hair was evaluated according to the following evaluation methods.

Results obtained are shown in Table 4.

Evaluation Methods (1) To 20 g (length: 15 cm) of hair shampooed, 4 g of the hair treatment composition was applied, which was left to stand at 40° C. for 20 minutes, followed by rinsing with running water and then drying. This was sampled as hair immediately after being treated. The feel and softness of the hair was evaluated by five specialist panelists according to the following criteria.

Feel of the Hair
  Ranks and criteria:
    AA: Very smooth and readily separable with fingers.
    A: Smooth and readily separable with fingers.
    B: The hair is not smooth and is a little rough.
    C: The hair is squeaky and is fairly rough.
Softness of the Hair
  Ranks and criteria:
    AA: Very soft compared with untreated hair.
    A: Soft compared with untreated hair.
    B: A little soft compared with untreated hair.
    C: Substantially the same as untreated hair.

(2) Hair samples respectively treated with the hair treatment compositions were washed with a commercially available shampoo and then dried. This procedure of washing and drying was repeatedly followed four times in total, and the following evaluation was made on the basis of a control which is a sample not shampooed after treatment.

Feel of the Hair
  Ranks and criteria:
    A: The hair has no difference from the control.
    B: The hair is slightly less flexible and not better combed than the control.
    C: The hair is fairly less flexible and not better combed than the control.
Softness of the Hair
  Ranks and criteria:
    A: The hair is well as soft as the control.
    B: The hair is slightly bristlier than the control.
    C: The hair is fairly bristlier than the control.

TABLE 2

(amount in % by weight)

| | Examples | | | | | | |
|---|---|---|---|---|---|---|---|
| | 1 | 2 | 3 | 4 | 5 | 6 | 7 |
| N-hexylpyrrolidone: | 5.0 | 5.0 | 5.0 | 5.0 | 5.0 | 5.0 | 5.0 |
| Ethanol: | 30.0 | 30.0 | 30.0 | 30.0 | 30.0 | 30.0 | 30.0 |
| Polymer JR-400*1: | 0.3 | 0.3 | 0.3 | — | — | 0.3 | 0.3 |
| MARCOAT 100*2: | — | — | — | 0.3 | — | — | — |
| PLUS SIZE L-401*3: | — | — | — | — | 0.3 | — | — |
| SOFTAXOLINE CL*4: | 0.3 | — | — | 0.3 | 0.3 | 0.3 | 0.3 |
| SOFTAZOLINE LPB*5: | — | 0.3 | — | — | — | — | — |
| N-lauroyl-N-methyltaurine: | — | — | 0.3 | — | — | — | — |
| 90% Lactic acid: | 8.0 | 8.0 | 8.0 | 8.0 | 8.0 | — | — |
| Sodium lactate: | 1.0 | 1.0 | 1.0 | 1.0 | 1.0 | — | — |
| Citric acid: | — | — | — | — | — | 4.0 | — |
| Sodium citrate: | — | — | — | — | — | 0.1 | — |
| Monoethanolamine: | — | — | — | — | — | — | 3.0 |
| Ammonium chloride: | — | — | — | — | — | — | 3.0 |
| Water: | bal. | bal. | bal. | bal. | bal. | bal. | bal. |
| pH: | 3.6 | 3.5 | 3.5 | 3.6 | 3.6 | 2.9 | 9.2 |

Table 2, remarks:
*1: Cationized cellulose (available from Union Carbide)
*2: Dimethyldiallyammonium polymer (available from Merck & Co., Inc.)
*3: N-methacryloylethyl-N,N'-dimethylammonium-α-N-methylcarboxybetaine polymer (available from Goo Chemical Co., Ltd.)
*4: 2-Cocoyl-N-carboxymethyl-N-hydroxyethylimidazolinium betaine (available from Kawaken Fine Chemicals Co., Ltd.)
*5: N-lauroylamidopropyl betaine (available from Kawaken Fine Chemicals Co., Ltd.)

TABLE 3

(amount in % by weight)

| | Comparative Example | | | | |
|---|---|---|---|---|---|
| | 1 | 2 | 3 | 4 | 5 |
| N-hexylpyrrolidone: | — | 5.0 | — | — | — |
| Benzyl alcohol: | — | — | 5.0 | — | — |
| N-methylpyrrolidone: | — | — | — | 5.0 | — |
| N-ethylpyrrolidone: | — | — | — | — | 5.0 |
| Ethanol: | — | 30.0 | 30.0 | 30.0 | 30.0 |
| Polymer JR-400*1: | 0.3 | — | 0.3 | 0.3 | 0.3 |
| SOFTAZOLINE CL*2: | 0.3 | 0.3 | 0.3 | 0.3 | 0.3 |
| 90% Lactic acid: | 8.0 | 8.0 | 8.0 | 8.0 | 8.0 |

TABLE 3-continued (amount in % by weight)

| | Comparative Example | | | | |
|---|---|---|---|---|---|
| | 1 | 2 | 3 | 4 | 5 |
| Sodium lactate: | 1.0 | 1.0 | 1.0 | 1.0 | 1.0 |
| Water: | bal. | bal. | bal. | bal. | bal. |
| pH | 3.6 | 3.6 | 3.6 | 3.6 | 3.6 |

Table 3, remarks:
*1: Cationized cellulose (available from Union Carbide)
*2: 2-Cocoyl-N-carboxymethyl-N-hydroxyethylimidazolinium betaine (available from Kawaken Fine Chemicals Co., Ltd.)

TABLE 4

| | Example | | | | | | | Comparative Example | | | | |
|---|---|---|---|---|---|---|---|---|---|---|---|---|
| | 1 | 2 | 3 | 4 | 5 | 6 | 7 | 1 | 2 | 3 | 4 | 5 |
| (Immediately after treatment) | | | | | | | | | | | | |
| Feel of the hair: | AA | AA | AA | AA | AA | AA | AA | A | B | B | B | B |
| Softness of the hair: | AA | AA | A | AA | AA | AA | AA | A | B | B | B | B |
| (After shampooing four times) | | | | | | | | | | | | |
| Feel of the hair: | A | A | A | A | A | A | A | C | C | C | C | C |
| Softness of the hair: | A | A | A | A | A | A | A | C | C | C | C | C |

As can be seen from Table 4, the hair treatment compositions of Examples 1 to 7, in which the components (A) and (B) are used in combination, show satisfactory results on the feel and softness of the hair not only immediately after treatment but also after shampooing four times.

On the other hand, in the case of the hair treatment composition of Comparative Example 1, in which the component (A) Is not contained, it shows satisfactory results more or less on the feel and softness of the hair immediately after treatment, though a little inferior to the results in Examples 1 to 7, but shows unsatisfactory results on those after shampooing four times. In the case of the hair treatment composition of Comparative Example 2, in which the component (B) is not contained, it shows more inferior results than the results in Comparative Example 1 on the feel and softness of the hair immediately after treatment and also shows unsatisfactory results on those after shampooing four times.

In the case of the hair treatment compositions in which the component (A) is replaced with benzyl alcohol (Comparative Example 3), N-methylpyrrolidone (Comparative Example 4) or N-ethylpyrrolidone (Comparative Example 5), they show more inferior results than the results in Comparative Example 1 on the feel and softness of the hair immediately after treatment and also shows unsatisfactory results on those after shampooing four times.

Examples 8 to 13, Comparative Examples 6 to 10

Hair treatment compositions having the formulation as shown in Tables 5 and 6 were prepared by conventional methods.

In respect of each hair treatment composition thus obtained, the conditioning effect brought about when applied to the hair was evaluated in the same manner as in Example 1, according to the following evaluation methods.

Results obtained are shown in Table 7.

Evaluation Methods (1) To 20 g (length: 15 cm) of hair shampooed, 4 g of the hair treatment composition was applied, which was left to stand at 40° C. for 20 minutes, followed by rinsing with running water and then drying. This was sampled as hair immediately after being treated. The feel and softness of the hair was evaluated by five specialist panelists according to the following criteria.

Feel of the Hair
  Ranks and criteria:
    AA: Very smooth and readily separable with fingers.
    A: Smooth and readily separable with fingers.
    B: The hair is not smooth and is a little rough.
    C: The hair is squeaky and is fairly rough.
Softness of the Hair
  Ranks and criteria:
    AA: Very soft compared with untreated hair.
    A: Soft compared with untreated hair.
    B: A little soft compared with untreated hair.
    C: Substantially the same as untreated hair.

(2) Hair samples respectively treated with the hair treatment compositions were washed with a commercially available shampoo and then dried. This procedure of washing and drying was repeatedly followed four times in total, and the following evaluation was made on the basis of a control which is a sample not shampooed after treatment.

Feel of the Hair
  Ranks and criteria:
    A: The hair has no difference from the control.
    B: The hair is slightly less flexible and not better combed than the control.
    C: The hair is fairly less flexible and not better combed than the control.

Softness of the Hair
  Ranks and criteria:
  A: The hair is well as soft as the control.
  B: The hair is slightly bristlier than the control.
  C: The hair is fairly bristlier than the control.

TABLE 5

(amount in % by weight)

|  | Examples | | | | | |
|---|---|---|---|---|---|---|
|  | 8 | 9 | 10 | 11 | 12 | 13 |
| N-hexylpyrrolidone: | 5.0 | 5.0 | 5.0 | 5.0 | 5.0 | 5.0 |
| Ethanol: | 30.0 | 30.0 | 30.0 | 30.0 | 30.0 | 30.0 |
| Xanthane gum: | 0.15 | 0.15 | — | — | 0.15 | 0.15 |
| Carboxymethyl cellulose: | — | — | 0.3 | — | — | — |
| PLUS SIZE GK707*6: | — | — | — | 0.3 | — | — |
| Trimethylammonium stearyl chloride: | 0.3 | — | 0.3 | 0.3 | 0.3 | 0.3 |
| SOFTAZOLINE LPB*7: | — | 0.3 | — | — | — | — |
| 90% Lactic acid: | 8.0 | 8.0 | 8.0 | 8.0 | — | — |
| Sodium lactate: | 1.0 | 1.0 | 1.0 | 1.0 | — | — |
| Citric acid: | — | — | — | — | 4.0 | — |
| Sodium citrate: | — | — | — | — | 0.1 | — |
| Monoethanolamine: | — | — | — | — | — | 3.0 |
| Ammonium chloride: | — | — | — | — | — | 3.0 |
| Water: | bal. | bal. | bal. | bal. | bal. | bal. |
| pH | 3.5 | 3.5 | 3.5 | 3.5 | 2.9 | 9.2 |

Table 5, remarks:
*6: Acrylic acid/acrylate/methacrylate copolymer (available from Goo Chemical Co., Ltd.)
*7: N-lauroylamidopropyl betaine (available from Kawaken Fine Chemicals Co., Ltd.)

TABLE 6

(amount in % by weight)

|  | Comparative Example | | | | |
|---|---|---|---|---|---|
|  | 6 | 7 | 8 | 9 | 10 |
| N-hexylpyrrolidone: | — | 5.0 | — | — | — |
| Benzyl alcohol: | — | — | 5.0 | — | — |
| N-methylpyrrolidone: | — | — | — | 5.0 | — |
| N-ethylpyrrolidone: | — | — | — | — | 5.0 |
| Ethanol: | — | 30.0 | 30.0 | 30.0 | 30.0 |
| Xanthane gum: | 0.15 | — | 0.15 | 0.15 | 0.15 |
| Trimethylammonium stearyl chloride: | 0.3 | 0.3 | 0.3 | 0.3 | 0.3 |
| 90% Lactic acid: | 8.0 | 8.0 | 8.0 | 8.0 | 8.0 |
| Sodium lactate: | 1.0 | 1.0 | 1.0 | 1.0 | 1.0 |
| Water: | bal. | bal. | bal. | bal. | bal. |
| pH | 3.5 | 3.5 | 3.5 | 3.5 | 3.5 |

TABLE 7

|  | Example | | | | | | Comparative Example | | | | |
|---|---|---|---|---|---|---|---|---|---|---|---|
|  | 8 | 9 | 10 | 11 | 12 | 13 | 6 | 7 | 8 | 9 | 10 |
| (Immediately after treatment) | | | | | | | | | | | |
| Feel of the hair: | AA | AA | AA | AA | AA | AA | A | B | B | B | B |
| Softness of the hair: | AA | AA | A | AA | AA | AA | A | B | B | B | B |
| (After shampooing four times) | | | | | | | | | | | |
| Feel of the hair: | A | A | A | A | A | A | C | C | C | C | C |
| Softness of the hair: | A | A | A | A | A | A | C | C | C | C | C |

As can be seen from Table 7, the hair treatment compositions of Examples 8 to 13, in which the components (A) and (B) are used in combination, show satisfactory results on the feel and softness of the hair not only immediately after treatment but also after shampooing four times.

On the other hand, in the case of the hair treatment composition of Comparative Example 6, in which the component (A) is not contained, it shows satisfactory results more or less on the feel and softness of the hair immediately after treatment, though a little inferior to the results in Examples 8 to 13, but shows unsatisfactory results on those after shampooing four times. In the case of the hair treatment composition of Comparative Example 7, in which the component (B) is not contained, it shows more inferior results than the results in Comparative Example 6 on the feel and softness of the hair immediately after treatment and also shows unsatisfactory results on those after shampooing four times.

In the case of the hair treatment compositions in which the component (A) is replaced with benzyl alcohol (Comparative Example 8), N-methylpyrrolidone (Comparative Example 9) or N-ethylpyrrolidone (Comparative Example 10), they show more inferior results than the results in Comparative Example 6 on the feel and softness of the hair immediately after treatment and also shows unsatisfactory results on those after shampooing four times.

Examples 14 and 15, Comparative Examples 11 to 19

Hair dye compositions (Examples 14 and 15, Comparative Examples 11 to 19) were prepared by mixing the components as shown in Tables 8 or 9, and the pH of the resultant mixtures was adjusted to 4 using a lactic acid buffer solution.

TABLE 8

(amount in % by weight)

|  | Example | |
|---|---|---|
| Components | 14 | 15 |
| (Acid dye) | | |
| Black No. 401: | 0.5 | 0.5 |
| (Penetration promoter) | | |
| N-hexylpyrrolidone: | 7.0 | 7.0 |
| Benzyl alcohol: | — | — |
| Diethylene glycol monoethyl ether: | — | — |

TABLE 8-continued (amount in % by weight)

| | Example | |
|---|---|---|
| Components | 14 | 15 |
| (Water-soluble macromolecule) | | |
| Carboxymethyl cellulose: | 1.0 | 1.0 |
| (Penetration promoting auxiliary) | | |
| Ethylene carbonate: | 10 | — |
| Propylene carbonate: | — | 10 |
| Ethanol: | 10 | 10 |
| Water: | balance | balance |

TABLE 9

(amount in % by weight)

| | Comparative Example | | | | | | | | |
|---|---|---|---|---|---|---|---|---|---|
| | 11 | 12 | 13 | 14 | 15 | 16 | 17 | 18 | 19 |
| (Acid dye) | | | | | | | | | |
| Black No. 401: | 0.5 | 0.5 | 0.5 | 0.5 | 0.5 | 0.5 | 0.5 | 0.5 | 0.5 |
| (Penetration promoter) | | | | | | | | | |
| N-hexylpyrrolidone: | 7.0 | — | — | — | — | — | — | — | — |
| Benzyl alcohol: | — | 7.0 | — | — | 7.0 | — | — | — | — |
| Diethylene glycol monoethyl ether: | — | — | 7.0 | — | — | 7.0 | — | — | — |
| N-methylpyrrolidone: | — | — | — | — | — | — | — | 7.0 | — |
| N-ethylpyrrolidone: | — | — | — | — | — | — | — | — | 7.0 |
| (Water-soluble macromolecule) | | | | | | | | | |
| Carboxymethyl cellulose: | 1.0 | 1.0 | 1.0 | 1.0 | 1.0 | 1.0 | 1.0 | 1.0 | 1.0 |
| (Penetration promoting auxiliary) | | | | | | | | | |
| Ethylene carbonate: | — | — | — | — | 10 | 10 | 10 | — | 10 |
| Propylene carbonate: | — | — | — | — | — | — | — | 10 | — |
| Ethanol: | 10 | 10 | 10 | 10 | 10 | 10 | 10 | 10 | 10 |
| Water: | bal. | bal. | bal. | bal. | bal. | bal. | bal. | bal. | bal. |

Each hair dye composition thus obtained was applied to grizzled human hair and then left to stand at 30° C. for 30 minutes. Thereafter, the hair was washed with a usual shampoo, followed by drying, and the dyeing properties and the flexibleness of the hair thus treated were organoleptically evaluated.

Results obtained are shown in Table 10. In the table, symbol "AA" denotes a very good instance; "A" a good instance; "B", an ordinary instance; and "C", a poor instance.

TABLE 10

| | Dyeing properties | Flexibleness of the hair |
|---|---|---|
| Example: | | |
| 14 | AA | A |
| 15 | AA | A |
| Comparative Example: | | |
| 11 | A | A |
| 12 | B | C |
| 13 | C | A |
| 14 | C | C |

TABLE 10-continued

| | Dyeing properties | Flexibleness of the hair |
|---|---|---|
| 15 | A | C |
| 16 | C | A |
| 17 | C | C |
| 18 | B | C |
| 19 | B | C |

As can be seen from the results shown in Table 10, the hair dye compositions of Examples 14 and 15, in which N-hexylpyrrolidone is used as the penetration promoter and ethylene carbonate or propylene carbonate is used as the penetration promoting auxiliary, show good results on the dyeing properties and the flexibleness of the hair.

On the other hand, in the case of the hair dye composition of Comparative Example 11, having the same formulation as Examples 14 and 15 except for using no penetration promoting auxiliary, it shows results inferior to the cases of Examples 14 and 15.

In the case when benzyl alcohol is used (Comparative Examples 12 and 15), the dyeing properties lower unless the penetration promoting auxiliary is used, also showing unsatisfactory results on the flexibleness of the hair. In the case when diethylene glycol monoethyl ether is used (Comparative Examples 13 and 16), good results are shown on the flexibleness of the hair without regard to whether or not the penetration promoting auxiliary is used, but unsatisfactory results on the dyeing properties. In the case when N-methylpyrrolidone or N-ethylpyrrolidone is used (Comparative Examples 18 and 16), the dyeing properties lower even when the penetration promoting auxiliary is used, also showing unsatisfactory results on the flexibleness of the hair.

In the case when the penetration promoter is not used (Comparative Examples 14 and 17), unsatisfactory results are shown on both the dyeing properties and the flexibleness of the hair without regard to whether or not the penetration promoting auxiliary is used.

Examples 16 to 18

Hair dye compositions (Examples 16 to 18) were prepared by mixing the components as shown in Table 11, and the pH of the resultant mixtures was adjusted to 3 using a lactic acid/citric acid buffer solution.

With regard to the hair dye compositions thus obtained, the dyeing properties and the flexibleness of the hair were organoleptically evaluated in the same manner as in Example 14.

Results obtained are shown in Table 11.

TABLE 11

(amount in % by weight)

| Components | Example 16 | Example 17 | Example 18 |
|---|---|---|---|
| (Acid dye) | | | |
| Orange No. 205: | 0.2 | — | 0.2 |
| Violet No. 401: | — | 0.2 | — |
| (Penetration promoter) | | | |
| N-hexylpyrrolidone: | 5.0 | 5.0 | 5.0 |
| (Water-soluble macromolecule) | | | |
| Xanthane gum: | 1.0 | — | 1.0 |
| Hydroxyethyl cellulose: | — | 1.0 | — |
| (Penetration promoting auxiliary) | | | |
| Propylene carbonate: | 15 | 15 | 15 |
| Ethanol: | 10 | 10 | — |
| Water: | bal. | bal. | bal. |
| (Evaluation) | | | |
| Dyeing properties: | AA | AA | AA |
| Flexibleness of the hair: | A | A | A |

As can be seen from the results shown in Table 11, the hair dye compositions of Examples 16 to 18, in which N-hexylpyrrolidone is used as the penetration promoter, show good results on both the dyeing properties and the flexibleness of the hair even when the acid dye is different.

Example 19

A black hair-dye composition was prepared by mixing the components as shown in Table 12, and the pH of the resultant mixture was adjusted to 2.8 using a citric acid/sodium citrate buffer solution.

With regard to the hair dye composition thus obtained, the dyeing properties and the flexibleness of the hair were organoleptically evaluated in the same manner as in Example 14. As a result, like Example 14, preferable results were obtained on both the dyeing properties and the flexibleness of the hair.

TABLE 12

| Components | Amount (wt. %) |
|---|---|
| (Acid dye) | |
| Black No. 401: | 0.1 |
| Violet No. 401: | 0.1 |
| (Penetration promoter) | |
| N-benzylpyrrolidone: | 10 |
| (Water-soluble macromolecule) | |
| Hydroxyethyl cellulose: | 0.5 |

TABLE 12-continued

| Components | Amount (wt. %) |
|---|---|
| (Penetration promoting auxiliary) | |
| Ethylene carbonate: | 20 |
| Ampholytic surfactant: | 0.3 |
| (SOFTAZOLINE CL; available from Kawaken Fine Chemicals Co., Ltd.)) | |
| Water: | balance |
| Perfume: | appropriate quantity |

Example 20

A brown hair-dye composition was prepared by mixing the components as shown in Table 13, and the pH of the resultant mixture was adjusted to 3.3 using a citric acid/sodium citrate buffer solution.

With regard to the hair dye composition thus obtained, the dyeing properties and the flexibleness of the hair were organoleptically evaluated in the same manner as in Example 14. As a result, like Example 14, preferable results were obtained on both the dyeing properties and the flexibleness of the hair.

TABLE 13

| Components | Amount (wt. %) |
|---|---|
| (Acid dye) | |
| Violet No. 401: | 0.07 |
| Orange No. 205: | 0.2 |
| Red No. 204: | 0.01 |
| Black No. 401: | 0.03 |
| (Penetration promoter) | |
| N-phenetylpyrrolidone: | 5 |
| (Water-soluble macromolecule) | |
| Hydroxyethyl cellulose: | 1.5 |
| (Penetration promoting auxiliary) | |
| Propylene carbonate: | 15 |
| 1,3-Butanediol: | 5 |
| Water: | balance |
| Perfume: | appropriate quantity |

Possibility of Industrial Application

The hair treatment composition of the present invention can impart a sufficient conditioning effect to the hair and can maintain its conditioning effect over a long period of time. In particular, it can give variations of color tones, has superior dyeing properties, can impart a good feel to the hair and also has a high safety to the hair and the skin.

What is claimed is:

1. A hair treatment composition comprising the following components (A) and (B):

(A) a compound of Formula (1)

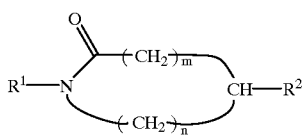
(1)

wherein $R^1$ represents (a) a hydrogen atom, (b) a straight-chain, branched or cyclic alkyl group or alkenyl group having 3 to 8 carbon atoms, (c) an aryl group or (d) a straight-chain, branched or cyclic alkyl group or alkenyl group having 1 to 8 carbon atoms, having in its backbone chain or side chain a substituent selected from the group consisting of an aryl group, a hydroxyl group, an ether group, an amide group, a carbonyl group and a carboxyl group; $R^2$ represents (a) a hydrogen atom, (b) a straight-chain, branched or cyclic alkyl group or alkenyl group having 1 to 8 carbon atoms, (c) an aryl group or (d) a straight-chain, branched or cyclic alkyl group or alkenyl group having 1 to 8 carbon atoms, having in its backbone chain or side chain a substituent selected from the group consisting of an aryl group, a hydroxyl group, an ether group, an amide group, a carbonyl group and a carboxyl group, provided that $R^1$ and $R^2$ are not hydrogen atoms at the same time; and n and m are integers that satisfy $2 \leq n+m \leq 4$;

(B) a water-soluble macromolecule, and (C) an acid dye.

2. The hair treatment composition according to claim 1, wherein the component (A) is contained in an amount of from 0.01 to 30% by weight and the component (B) is contained in an amount of from 0.01 to 20% by weight.

3. The hair treatment composition according to claim 1, wherein the compound of Formula (1) is N-butylpyrrolidone, N-pentylpyrrolidone, N-hexylpyrrolidone, N-heptylpyrrolidone, N-octylpyrrolidone, N-(2-ethylhexyl)pyrrolidone, N-benzylpyrrolidone or N-phenetylpyrrolidone.

4. The hair treatment composition according to claim 3, wherein the compound of Formula (1) is N-hexylpyrrolidone.

5. The hair treatment composition according to claim 1, wherein the component (A) is contained in an amount of from 0.01 to 30% by weight, the component (B) is contained in an amount of from 0.05 to 20% by weight, and the component (C) is contained in an amount of from 0.0001 to 10% by weight.

6. The hair treatment composition according to claim 1, which further comprises at least one of ethylene carbonate and propylene carbonate as component (D).

7. The hair treatment composition according to claim 6, wherein the component (D) is contained in an amount of from 0.1 to 30% by weight.

* * * * *